(12) United States Patent
Obika et al.

(10) Patent No.: US 11,286,275 B2
(45) Date of Patent: Mar. 29, 2022

(54) NUCLEIC ACID COMPOUND AND OLIGONUCLEOTIDE

(71) Applicant: Osaka University, Suita (JP)

(72) Inventors: Satoshi Obika, Suita (JP); Kosuke Ito, Suita (JP); Takaki Habuchi, Suita (JP); Masahiko Horiba, Suita (JP)

(73) Assignee: Osaka University, Suita (JP)

( * ) Notice: Subject to any disclaimer, the term of this patent is extended or adjusted under 35 U.S.C. 154(b) by 136 days.

(21) Appl. No.: 16/487,785

(22) PCT Filed: Feb. 20, 2018

(86) PCT No.: PCT/JP2018/006062
§ 371 (c)(1),
(2) Date: Aug. 21, 2019

(87) PCT Pub. No.: WO2018/155451
PCT Pub. Date: Aug. 30, 2018

(65) Prior Publication Data
US 2020/0055890 A1    Feb. 20, 2020

(30) Foreign Application Priority Data
Feb. 21, 2017   (JP) .............................. JP2017-030490

(51) Int. Cl.
C07H 21/02 (2006.01)
A61K 48/00 (2006.01)
C07H 19/10 (2006.01)
C12N 15/113 (2010.01)

(52) U.S. Cl.
CPC ............. *C07H 19/10* (2013.01); *C07H 21/02* (2013.01); *C12N 15/113* (2013.01); *C12N 2310/11* (2013.01)

(58) Field of Classification Search
CPC .................................................. C12N 15/113
See application file for complete search history.

(56) References Cited

U.S. PATENT DOCUMENTS

| | | |
|---|---|---|
| 2004/0033973 A1 | 2/2004 | Manoharan et al. |
| 2012/0208991 A1 | 8/2012 | Obika et al. |
| 2015/0266917 A1* | 9/2015 | Obika .................... C07H 23/00 536/23.1 |
| 2017/0044528 A1 | 2/2017 | Obika et al. |

FOREIGN PATENT DOCUMENTS

| | | |
|---|---|---|
| WO | WO 2004/035819 A2 | 4/2004 |
| WO | WO 2004/044245 A1 | 5/2004 |
| WO | WO 2011/052436 A1 | 5/2011 |
| WO | WO 2014/046212 A1 | 3/2014 |
| WO | WO 2015/125783 A1 | 8/2015 |
| WO | WO 2017/018360 A1 | 2/2017 |

OTHER PUBLICATIONS

Carlucci et al., "Chemical Synthesis of LNA-2-thiouridine and Its Influence on Stability and Selectivity of Oligonucleotide Binding to RNA," *Biochemistry*, 48(46): 10882-10893 (2009).
Habuchi et al., "Synthesis and property of scpBNA-2-thiothymine," *137th Annual Meeting of the Pharmaceutical Society of Japan*, Abstract 27U-am09S (2017).
Hassan et al., "High Fidelity of Base Pairing by 2-Selenothymidine in DNA," *J. Am. Chem. Soc.*, 132(7): 2120-2121 (2010).
Mitsuoka et al., "A bridged nucleic acid, 2',4'-BNA$^{coc}$: synthesis of fully modified oligonucleotides bearing thymine, 5-methylcytosine, adenine and guanine 2',4'-BNA$^{coc}$ monomers and RNA-selective nucleic-acid recognition," *Nucleic Acids Res.*, 37(4): 1225-1238 (2009).
Sintim et al., "Enhanced Base Pairing and Replication Efficiency of Thiothymidines, Expanded-size Variants of Thymidine," *J. Am. Chem. Soc.*, 128(2): 396-397 (2006).
Japanese Patent Office, International Search Report in International Patent Application No. PCT/JP2018/006062 (dated Mar. 27, 2018).
Horiba et al., "Synthesis of scpBNA-$^m$C, -A, and -G Monomers and Evaluation of the Binding Affinities of scpBNA-Modified Oligonucleotides towards Complementary ssRNA and ssDNA," *J. Org. Chem.*, 81(22): 11000-11008 (2016).
Hughesman, "Role of the Heat Capacity Change in Understanding and Modeling Melting Thermodynamics of Complementary Duplexes Containing Standard and Nucleobase-Modified LNA," *Biochemistry*, 50(23): 5354-5368 (2011).
Yahara et al., "Amido-Bridged Nucleic Acids (AmNAs): Synthesis, Duplex Stability, Nuclease Resistance, and in Vitro Antisense Potency," *ChemBioChem*, 13(17): 2513-2516 (2012).
European Patent Office, Extended European Search Report in European Patent Application No. 18757437.1 (dated Dec. 8, 2020).

\* cited by examiner

*Primary Examiner* — Amy H Bowman
(74) *Attorney, Agent, or Firm* — Leydig, Voit & Mayer, Ltd.

(57) ABSTRACT

The present invention aims to provide a nucleic acid compound that hardly forms non-Watson-Crick base pairs, and an oligonucleotide containing the nucleic acid compound and showing reduced non-specific binding with nucleic acids other than the target nucleic acid. The nucleic acid compound according to the present invention is characterized in that the 2-position carbonyl group of the pyrimidine base is functionally converted ($X^1$ and $X^2$ are each independently S or Se), and that the 2'-position and the 4'-position are bridged in a particular structure. The oligonucleotide according to the present invention is characterized in that at least one of thymidine and uridine is the nucleic acid compound.

15 Claims, 2 Drawing Sheets
Specification includes a Sequence Listing.

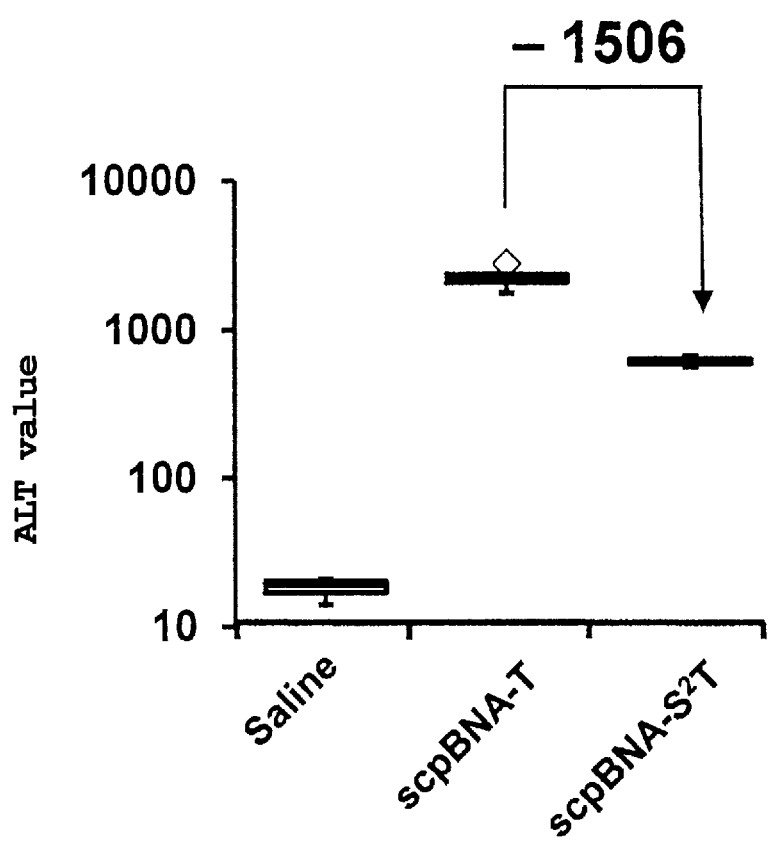

SEQUENCE LISTING

<160> NUMBER OF SEQ ID NOS: 14

<210> SEQ ID NO 1
<211> LENGTH: 12
<212> TYPE: RNA
<213> ORGANISM: Artificial Sequence
<220> FEATURE:
<223> OTHER INFORMATION: Synthetic Target strand
<220> FEATURE:
<221> NAME/KEY: misc_feature
<222> LOCATION: (7)..(7)
<223> OTHER INFORMATION: n is a, c, g, or u

<400> SEQUENCE: 1
agcaaanaac gc                                                          12

<210> SEQ ID NO 2

-continued

```
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (6)..(6)
<223> OTHER INFORMATION: n is for 2',4'-cyclopropylene-O-bridged
      2-thiothymidine

<400> SEQUENCE: 2
gcgttntttg ct                                                          12

<210> SEQ ID NO 3
<211> LENGTH: 12
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (6)..(6)
<223> OTHER INFORMATION: n is for 2',4'-cyclopropylene-O-bridged
      2-selenothymidine

<400> SEQUENCE: 3
gcgttntttg ct                                                          12

<210> SEQ ID NO 4
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-CH2-O-bridged thymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-CH2-O-bridged thymidine
<220> FEATURE:
<221> NAME/KEY: modified_base
<222> LOCATION: (13)..(14)
<223> OTHER INFORMATION: n is for 2',4'-CH2-O-bridged guanosine

<400> SEQUENCE: 4
nnntctttac cnnn                                                        14

<210> SEQ ID NO 5
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-cyclopropylene-O-bridged
```

```
        2-thiothymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-cyclopropylene-O-bridged
        2-thiothymidine
<220> FEATURE:
<221> NAME/KEY: modified_base
<222> LOCATION: (13)..(14)
<223> OTHER INFORMATION: n is for 2',4'-CH2-O-bridged guanosine

<400> SEQUENCE: 5
nnntctttac cnnn                                                       14

<210> SEQ ID NO 6
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged adenosine
<220> FEATURE:
<221> NAME/KEY: modified_base
<222> LOCATION: (2)..(3)
<223> OTHER INFORMATION: n is for 2',4'-CH2-O-bridged guanosine
<220> FEATURE:
<221> NAME/KEY: modified_base
<222> LOCATION: (12)..(12)
<223> OTHER INFORMATION: n is for 2',4'-CH2-O-bridged thymidine
<220> FEATURE:
<221> NAME/KEY: modified_base
<222> LOCATION: (13)..(13)
<223> OTHER INFORMATION: n is for 2',4'-CH2-O-bridged 5-methylcytidine
<220> FEATURE:
<221> NAME/KEY: modified_base
<222> LOCATION: (14)..(14)
<223> OTHER INFORMATION: n is for 2',4'-CH2-O-bridged thymidine

<400> SEQUENCE: 6
nnntgctttg gnnn                                                       14

<210> SEQ ID NO 7
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged adenosine
<220> FEATURE:
<221> NAME/KEY: modified_base
<222> LOCATION: (2)..(3)
<223> OTHER INFORMATION: n is for 2',4'-CH2-O-bridged guanosine
<220> FEATURE:
<221> NAME/KEY: modified_base
<222> LOCATION: (12)..(12)
<223> OTHER INFORMATION: n is for 2',4'-cyclopropylene-O-bridged
        2-thiothymidine
<220> FEATURE:
<221> NAME/KEY: modified_base
<222> LOCATION: (13)..(13)
<223> OTHER INFORMATION: n is for 2',4'-CH2-O-bridged 5-methylcytidine
<220> FEATURE:
<221> NAME/KEY: modified_base
<222> LOCATION: (14)..(14)
<223> OTHER INFORMATION: n is for 2',4'-CH2-O-bridged thymidine
```

<400> SEQUENCE: 7
nnntgctttg gnnn    14

<210> SEQ ID NO 8
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-cyclopropylene-O-bridged
     thymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-CH2-O-bridged thymidine
<220> FEATURE:
<221> NAME/KEY: modified_base
<222> LOCATION: (13)..(14)
<223> OTHER INFORMATION: n is for 2',4'-CH2-O-bridged adenosine

<400> SEQUENCE: 8
nnncgcatgc cnnn    14

<210> SEQ ID NO 9
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-cyclopropylene-O-bridged
     2-thiothymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-CH2-O-bridged thymidine
<220> FEATURE:
<221> NAME/KEY: modified_base
<222> LOCATION: (13)..(14)
<223> OTHER INFORMATION: n is for 2',4'-CH2-O-bridged adenosine

<400> SEQUENCE: 9
nnncgcatgc cnnn    14

<210> SEQ ID NO 10
<211> LENGTH: 12
<212> TYPE: DNA
<213> ORGANISM: Artificial Sequence
<220> FEATURE:
<223> OTHER INFORMATION: Synthetic Sequence
<220> FEATURE:

```
<221> NAME/KEY: modified_base
<222> LOCATION: (6)..(6)
<223> OTHER INFORMATION: n is for 2',4'-cyclopropylene-O-bridged
      thymidine

<400> SEQUENCE: 10
gcgttntttg ct                                                         12

<210> SEQ ID NO 11
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-cyclopropylene-O-bridged
      thymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-cyclopropylene-O-bridged
      thymidine
<220> FEATURE:
<221> NAME/KEY: modified_base
<222> LOCATION: (13)..(14)
<223> OTHER INFORMATION: n is for 2',4'-CH2-O-bridged guanosine

<400> SEQUENCE: 11
nnntctttac cnnn                                                       14

<210> SEQ ID NO 12
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged guanosine
<220> FEATURE:
<221> NAME/KEY: modified_base
<222> LOCATION: (2)..(2)
<223> OTHER INFORMATION: n is for 2',4'-C(=O)-N(-CH3)-bridged thymidine
<220> FEATURE:
<221> NAME/KEY: modified_base
<222> LOCATION: (3)..(3)
<223> OTHER INFORMATION: n is for 2',4'-CH2-O-bridged 5-methylcytidine
<220> FEATURE:
<221> NAME/KEY: modified_base
<222> LOCATION: (12)..(12)
<223> OTHER INFORMATION: n is for 2',4'-C(=O)-N(-CH3)-bridged thymidine
<220> FEATURE:
<221> NAME/KEY: modified_base
<222> LOCATION: (13)..(14)
<223> OTHER INFORMATION: n is for 2',4'-CH2-O-bridged guanosine

<400> SEQUENCE: 12
nnntctttac cnnn                                                       14

<210> SEQ ID NO 13
<211> LENGTH: 14
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged adenosine
<220> FEATURE:
<221> NAME/KEY: modified_base
<222> LOCATION: (2)..(3)
<223> OTHER INFORMATION: n is for 2',4'-CH2-O-bridged guanosine
<220> FEATURE:
<221> NAME/KEY: modified_base
<222> LOCATION: (12)..(12)
<223> OTHER INFORMATION: n is for 2',4'-cyclopropylene-O-bridged-
      thymidine
<220> FEATURE:
<221> NAME/KEY: modified_base
<222> LOCATION: (13)..(13)
<223> OTHER INFORMATION: n is for 2',4'-CH2-O-bridged 5-methylcytidine
<220> FEATURE:
<221> NAME/KEY: modified_base
<222> LOCATION: (14)..(14)
<223> OTHER INFORMATION: n is for 2',4'-CH2-O-bridged thymidine

<400> SEQUENCE: 13
nnntgctttg gnnn                                                        14

<210> SEQ ID NO 14
<211> LENGTH: 14
<212> TYPE: DNA
<213> ORGANISM: Artificial Sequence
<220> FEATURE:
<223> OTHER INFORMATION: Synthetic Sequence
<220> FEATURE:
<221> NAME/KEY: modified_base
<222> LOCATION: (1)..(1)
<223> OTHER INFORMATION: n is for 2',4'-CH2-O-bridged adenosine
<220> FEATURE:
<221> NAME/KEY: modified_base
<222> LOCATION: (2)..(3)
<223> OTHER INFORMATION: n is for 2',4'-CH2-O-bridged guanosine
<220> FEATURE:
<221> NAME/KEY: modified_base
<222> LOCATION: (12)..(12)
<223> OTHER INFORMATION: n is for 2',4'-C(=O)-N(-CH3)-bridged thymidine
<220> FEATURE:
<221> NAME/KEY: modified_base
<222> LOCATION: (13)..(13)
<223> OTHER INFORMATION: n is for 2',4'-CH2-O-bridged 5-methylcytidine
<220> FEATURE:
<221> NAME/KEY: modified_base
<222> LOCATION: (14)..(14)
<223> OTHER INFORMATION: n is for 2',4'-CH2-O-bridged thymidine

<400> SEQUENCE: 14
nnntgctttg gnnn                                                        14
```

NUCLEIC ACID COMPOUND AND OLIGONUCLEOTIDE

CROSS-REFERENCE TO RELATED APPLICATIONS

This patent application is the U.S. national phase of International Patent Application No. PCT/JP2018/006062, filed Feb. 20, 2018, which claims the benefit of Japanese Patent Application No. 2017-030490, filed Feb. 21, 2017, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,817 bytes ASCII (Text) file named "744816SequenceListing.txt," created Aug. 20, 2019.

TECHNICAL FIELD

The present invention relates to a nucleic acid compound that hardly forms non-Watson-Crick base pairs and an oligonucleotide containing the nucleic acid compound and showing reduced non-specific binding with nucleic acids other than the target nucleic acid.

BACKGROUND ART

It has been clarified by Watson and Crick that the chromosome is composed of DNA double strands. In addition, a double strand is partially formed in the mRNA molecule. Furthermore, various therapeutic methods utilizing interaction between nucleic acids have been developed in recent years. For example, an antisense oligonucleotide binds to a single-stranded portion of RNA related to a disease to form a double strand and inhibits its action. Typically, a method is known in which complementary DNA is bound to a single-stranded portion of mRNA to form a double strand, and this part is hydrolyzed and cleaved with RNaseH.

In addition, a method is also known in which a triplex strand is formed by an antigene complementary to a gene related to a disease and a DNA double strand of the gene, and transcription from DNA to mRNA is inhibited. siRNA specifically cleaves target mRNA by RNA interference.

The above-mentioned interaction between nucleic acid strands is based on hydrogen bonds between nucleic acid bases. For example, the interaction between adenosine adenine and thymidine thymine is shown below.

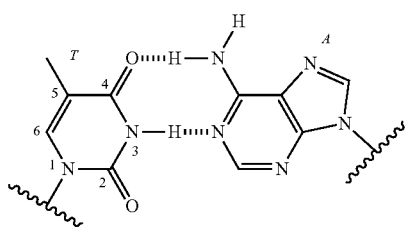

Watson-Crick base pair

However, since the interaction between thymine and guanine described below is also relatively stable thermodynamically, a non-Watson-Crick base pair called a wobble base pair is sometimes formed. Such wobble base pair may cause binding of the above-mentioned antisense oligonucleotide or the like to a nucleic acid other than the original target nucleic acid, and may lead to unexpected expression of gene or suppression of expression of important gene. Such phenomenon is called an off-target effect and may cause serious side effects (non-patent document 1).

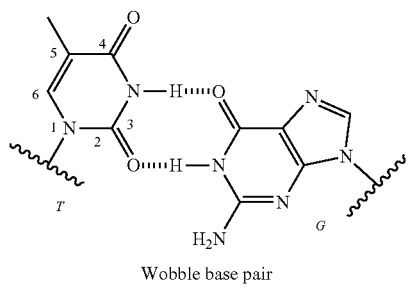

Wobble base pair

Thus, it has been clarified that the hydrogen binding strength with guanine can be reduced by converting the 2-position carbonyl group of thymine to a thiocarbonyl group, whereby formation of G-T non-Watson-Crick base pair can be suppressed (non-patent document 2).

While nucleic acid drugs such as the above-mentioned antisense oligonucleotide and the like have an advantage of high specificity, they have a problem of insufficient stability in vivo since they serve as nuclease substrates. In addition, the nucleoside moiety in the nucleic acid has an N-type or S-type structure, and this structure also affects the interaction between nucleic acid bases. Therefore, the present inventors' research group has developed a technique for bridging the 2'-position and the 4'-position of the nucleic acid, stabilizing the nucleic acid conformation, increasing the nuclease resistance, and increasing the affinity for the target nucleic acid (patent documents 1-5).

DOCUMENT LIST

Patent Documents patent document 1: WO 2011/052436
patent document 2: WO 2014/046212
patent document 3: WO 2014/112463
patent document 4: WO 2015/125783
patent document 5: WO 2016/017422

Non-Patent Document non-patent document 1: Obika, S et al., Nucleic Acids Res., 37, pp. 1225-1238 (2009)
non-patent document 2: Herman. 0 et al., J. Am. Chem. Soc., 128, pp. 396-397 (2006)

SUMMARY OF THE INVENTION

Problems to be Solved by the Invention

As described above, it was known that formation of G-T non-Watson-Crick base pair can be suppressed by functionally converting the 2-position carbonyl group of thymine to a thiocarbonyl group. However, non-Watson-Crick type base pair is considered to be one of the causes of side effects caused by nucleic acid drugs, and a method for further suppressing the formation of non-Watson-Crick type base pair has been demanded.

It is therefore an object of the present invention is to provide a nucleic acid compound hardly forms non-Watson-Crick base pairs, and an oligonucleotide containing the nucleic acid compound and showing reduced non-specific binding with nucleic acids other than the target nucleic acid.

Means of Solving the Problems

The present inventors have conducted intensive studies in an attempt to solve the aforementioned problems and found that bridging of the 2'-position and 4'-position in the nucleic acid compound in the nucleic acid chain improves the affinity with the complementary nucleic acid chain, and that formation of non-Watson-Crick base pairs can be unexpectedly suppressed by bridging the 2'-position and the 4'-position in addition to the modification of the 2-position carbonyl group of thymine, which resulted in the completion of the present invention.

The present invention is described below.

[1] A nucleic acid compound represented by the following formula (I) or the following formula (II), or a salt thereof:

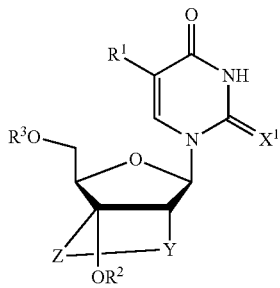
(I)

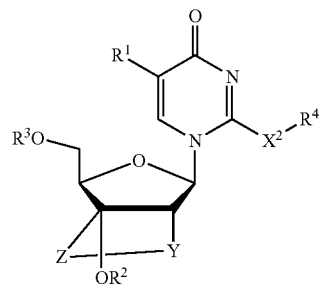
(II)

wherein
$X^1$ and $X^2$ are each independently S or Se,
Y is a guanidino group represented by any of the following formulas (III)-(VI), and Z is a single bond or a $C_{1-4}$ alkylene group,

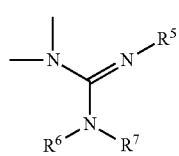
(III)

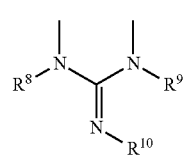
(IV)

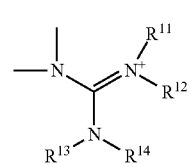
(V)

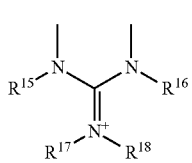
(VI)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, or Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the following formula (VII):

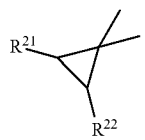
(VII)

wherein $R^{21}$ and $R^{22}$ are each independently H, a $C_{1-6}$ alkyl group, or $R^{21}$ and $R^{22}$ are optionally joined to form a $C_{1-4}$ alkylene group, or Y and Z are joined to form a —C(=O)—O— group or a —C(=O)—N($R^{20}$)— group ($R^{20}$ is H or a $C_{1-6}$ alkyl group),
$R^1$ is H or a $C_{1-6}$ alkyl group,
$R^2$ and $R^3$ are each independently H, a hydroxyl-protecting group, or a phosphate group represented by the following formula (VIII):

$$R^{23}-\underset{\underset{(Q)_n}{\overset{\|}{P}}}{\overset{|}{O}}-R^{24}$$
(VIII)

wherein Q is O or S, $R^{23}$ is H, a hydroxyl group, or a $C_{1-6}$ alkoxy group optionally substituted by a cyano group; $R^{24}$ is a hydroxyl group, a $C_{1-6}$ alkoxy group optionally substituted by a cyano group or an $NR^{25}R^{26}$ group wherein $R^{25}$ and $R^{26}$ are each independently H, a $C_{1-6}$ alkyl group or a 2-cyanoethyl group; and n is 0 or 1, and
$R^4$ is H, a $C_{1-6}$ alkyl group or a 2-cyanoethyl group.

[2] The nucleic acid compound of the above-mentioned [1] wherein Y is O and Z is a cyclopropyl group represented by the above-mentioned formula (VII), or a salt thereof.

[3] The nucleic acid compound of the above-mentioned [1] or [2] wherein $R^1$ is a methyl group, or a salt thereof.

[4] An oligonucleotide having one or more nucleic acid residues with a structure represented by the following formula (IX), or a pharmacologically acceptable salt thereof:

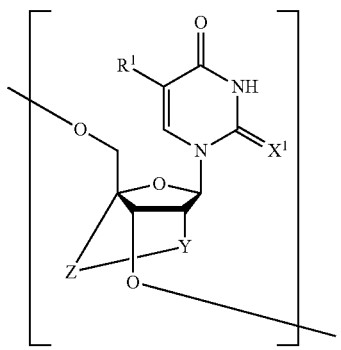

(IX)

wherein $X^1$ is S or Se,

Y is a guanidino group represented by any of the following formulas (III)-(VI), and Z is a single bond or a $C_{1-4}$ alkylene group,

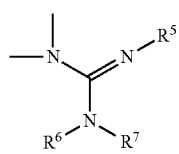

(III)

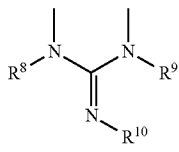

(IV)

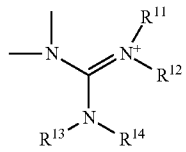

(V)

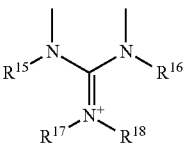

(VI)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, or Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the following formula (VII):

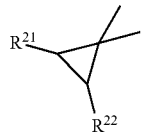

(VII)

wherein $R^{21}$ and $R^{22}$ are each independently H, a $C_{1-6}$ alkyl group, or $R^{21}$ and $R^{22}$ are optionally joined to form a $C_{1-4}$ alkylene group, or Y and Z are joined to form a —C(=O)—O— group or a —C(=O)—N($R^{20}$)— group ($R^{20}$ is H or a $C_{1-6}$ alkyl group), and $R^1$ is H or a $C_{1-6}$ alkyl group.

[5] The oligonucleotide of the above-mentioned [4] wherein Y is O and Z is a cyclopropyl group represented by the above-mentioned formula (VII), or a pharmacologically acceptable salt thereof.

[6] The oligonucleotide of the above-mentioned [4] or [5] wherein $R^1$ is a methyl group, or a pharmacologically acceptable salt thereof.

In this disclosure, the "$C_{1-6}$ alkyl group" is a linear or branched chain monovalent saturated aliphatic hydrocarbon group with a carbon number of not less than one and not more than 6. For example, methyl, ethyl, n-propyl, isopropyl, n-butyl, isobutyl, s-butyl, t-butyl, n-pentyl, n-hexyl and the like can be mentioned. Preferred is a $C_{1-4}$ alkyl group, more preferred is a $C_{1-2}$ alkyl group, most preferred is methyl.

The "$C_{3-10}$ cycloalkyl group" is a cyclic monovalent saturated aliphatic hydrocarbon group with a carbon number of not less than 3 and not more than 10. It is, for example, cyclopropyl, methylcyclopropyl, dimethylcyclopropyl, cyclobutyl, cyclopentyl, cyclohexyl, adamantyl or the like. Preferred is a $C_{3-6}$ cycloalkyl group.

Examples of the "amino-protecting group" include alkoxycarbonyl protecting groups such as t-butoxycarbonyl, methoxycarbonyl, ethoxycarbonyl and the like; arylmethoxycarbonyl protecting groups such as benzyloxycarbonyl, p-methoxybenzyloxycarbonyl, p-nitrobenzyloxycarbonyl, o-nitrobenzyloxycarbonyl and the like; arylmethyl protecting groups such as benzyl, 4-methoxybenzyl, triphenylmethyl and the like; alkanoyl protecting groups such as formyl, acetyl and the like; aroyl protecting groups such as benzoyl and the like; arylsulfonyl protecting groups such as 2,4-dinitrobenzenesulfonyl group o-nitrobenzenesulfonyl and the like, and the like.

The "$C_{1-4}$ alkylene group" is a linear or branched chain divalent saturated aliphatic hydrocarbon group with a carbon number of not less than one and not more than 4. It is, for example, methylene, ethylene, methylmethylene, n-propylene, methylethylene, n-butylene, methylpropylene, dimethylethylene or the like. It is preferably a $C_{1-2}$ alkylene group, more preferably methylene.

Examples of the "hydroxyl-protecting group" include alkanoyl protecting groups such as formyl, acetyl, propionyl and the like; aralkyl protecting groups such as benzyl, p-methoxybenzyl, p-nitrobenzyl and the like; silyl protecting groups such as trimethylsilyl, triethylsilyl, t-butyldimethylsilyl and the like; trityl protecting groups such as trityl, monomethoxytrityl, dimethoxytrityl and the like; alkoxyalkyl protecting groups such as methoxymethyl and the like; ether protecting groups such as tetrahydropyranyl (THP) and the like, and the like.

The "$C_{1-6}$ alkoxy group" is a linear or branched chain aliphatic hydrocarbonoxy group having not less than one and not more than 6 carbon atoms. It is, for example, methoxy, ethoxy, n-propoxy, isopropoxy, n-butoxy, isobutoxy, t-butoxy, n-pentoxy, n-hexoxy or the like, preferably a $C_{1-4}$ alkoxy group, more preferably a $C_{1-2}$ alkoxy group. The $C_{1-6}$ alkoxy group optionally substituted by a cyano group is preferably a 2-cyanoethoxy group.

The "salt of nucleic acid compound" is not particularly limited. Examples thereof include alkali metal salts such as sodium salt, potassium salt, lithium salt and the like; alkaline earth metal salts such as calcium salt and the like; magnesium salt; metal salts such as aluminum salt, iron salt, zinc salt, copper salt, nickel salt, cobalt salt and the like; inorganic amine salts such as ammonium salt and the like; organic amine salts such as t-octylamine salt, dibenzylamine salt, morpholine salt, glucosamine salt, phenylglycine alkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt and the like; hydrohalides such as hydrofluoride, hydrochloride, hydrobromide, hydroiodide and the like; inorganic acid salts such as nitrate, perchlorate, sulfate, phosphate and the like; lower alkanesulfonates such as methanesulfonate, trifluoromethanesulfonate, ethanesulfonate and the like; arylsulfonates such as benzenesulfonate, p-toluenesulfonate and the like; organic acid salts such as acetate, malate, fumarate, succinate, citrate, tartrate, oxalate, maleate and the like; amino acid salts such as glycine salt, lysine salt, arginine salt, ornithine salt, glutamate, aspartate and the like, and the like.

The "pharmacologically acceptable salt" is not particularly limited as long as it is harmless or less harmful to living organisms. Examples thereof include alkali metal salts such as sodium salt, potassium salt, lithium salt and the like; alkaline earth metal salts such as calcium salt and the like; magnesium salt; metal salts such as aluminum salt, iron salt, zinc salt, copper salt, nickel salt, cobalt salt and the like; inorganic amine salts such as ammonium salt and the like; organic amine salts such as t-octylamine salt, dibenzylamine salt, morpholine salt, glucosamine salt, phenylglycine alkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt and the like; hydrohalide such as hydrochloride, hydrobromide, hydroiodide and the like; inorganic acid salts such as nitrate, perchlorate, sulfate, phosphate and the like; lower alkanesulfonates such as methanesulfonate, trifluoromethanesulfonate, ethanesulfonate and the like; arylsulfonates such as benzenesulfonate, p-toluenesulfonate and the like; organic acid salts such as acetate, malate, fumarate, succinate, citrate, tartrate, oxalate, maleate and the like; and amino acid salts such as glycine salt, lysine salt, arginine salt, ornithine salt, glutamate, aspartate and the like.

In the above-mentioned formula (VIII), when Q=S and at least one of $R^{23}$ and $R^{24}$ is a hydroxyl group, the hydroxyl group may be —O⁻ and >P(=S)O⁻ is equivalent to >P(=O)S⁻.

Effect of the Invention

The nucleic acid compound according to the present invention is a thymidine or uridine derivative and hardly forms non-Watson-Crick base pairs because it maintains affinity for adenosine while showing remarkably reduced affinity for guanosine. As a result, oligonucleotide containing the nucleic acid compound according to the present invention hardly binds to nucleic acid chains other than its complementary chain. Therefore, the oligonucleotide according to the present invention resists side effects due to an off-target effect when utilized as an antisense oligonucleotide for the antisense method and the like, and is useful as an active ingredient of nucleic acid drugs.

BRIEF DESCRIPTION OF THE DRAWINGS

FIG. 3 is a graph showing the results of hepatotoxicity of antisense oligonucleic acid evaluated in the Example described later.

DESCRIPTION OF EMBODIMENTS

Figure 1:
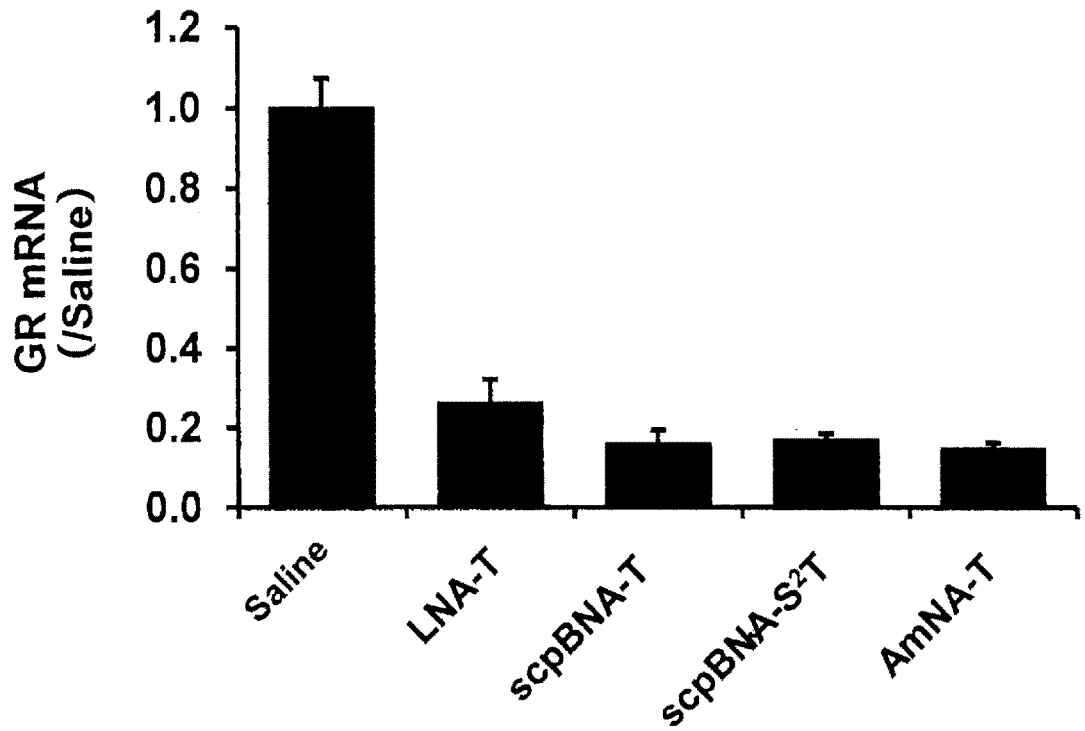
FIG. 1 is a graph showing the results of GR gene expression-suppressing activity evaluated in the Example described later.

Those of ordinary skill in the art can synthesize the nucleic acid compound according to the present invention from a known compound. For example, the 2-position carbonyl group of thymine or uracil can be converted to a thiocarbonyl group by the following scheme by reference to Sekine, M et al., J. Org. Chem., 68, pp. 9971-9982 (2003).

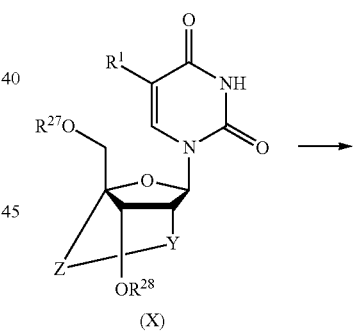

(X)

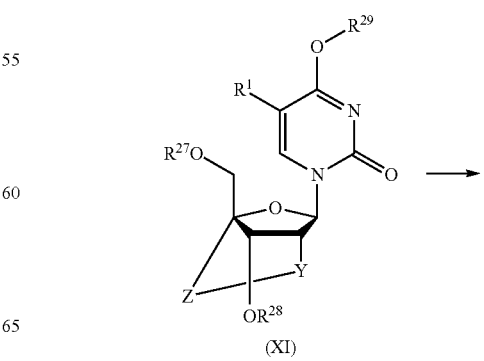

(XI)

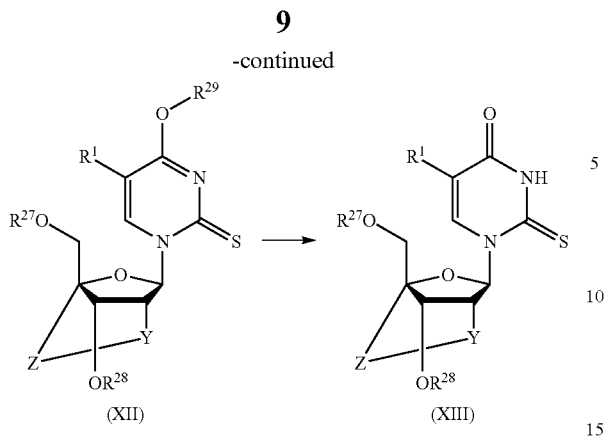

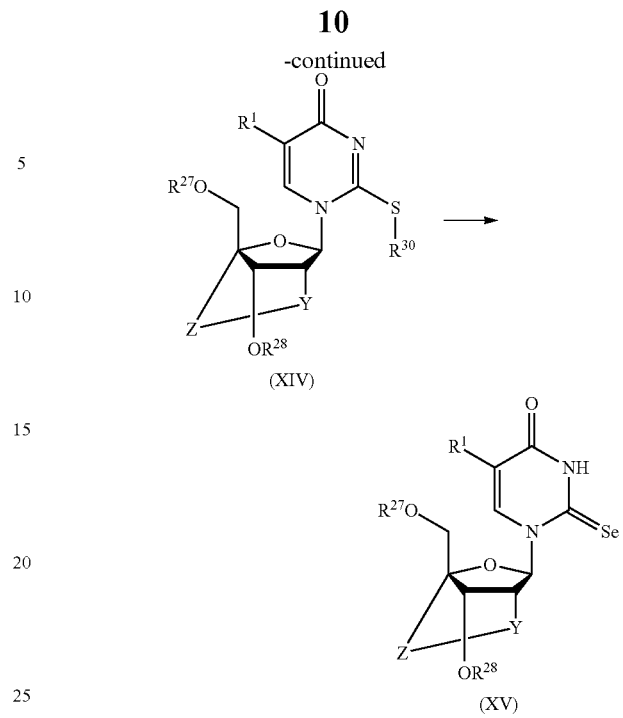

wherein Y, Z and $R^1$ are as defined above, $R^{27}$ and $R^{28}$ are each independently H or a hydroxyl-protecting group; and $R^{29}$ is a hydroxyl-protecting group.

The above-mentioned nucleic acid compound (X) wherein the 3'-position hydroxyl group and the 5'-position hydroxyl group are unprotected and at least one of the 3'-position hydroxyl group and the 5'-position hydroxyl group is protected is a known compound described in, for example, WO2014/046212, WO/2015/125783 and the like. Firstly, the 4-position carbonyl group in the pyrimidine moiety of the above-mentioned nucleic acid compound (X) is selectively protected with TPS by treating with 2,4,6-triisopropylbenzenesulfonyl chloride (TPSCl) in a solvent such as acetonitrile and the like, and the 4-position is selectively protected using a base and 2,6-dimethylphenol and the like to give nucleic acid compound (XI). In this case, nucleic acid compound (X) wherein both the 3'-position hydroxyl group and the 5'-position hydroxyl group are protected is preferably used. Then, using a Lawesson reagent, only the 2-position carbonyl group in the pyrimidine moiety of nucleic acid compound (XI) can be converted to a thiocarbonyl group. Lastly, the 4-position hydroxyl-protecting group in the pyrimidine moiety is removed, whereby nucleic acid compound (XIII) wherein the 2-position in the pyrimidine moiety is thiocarbonylated can be obtained.

As a method for selenizing the thiocarbonyl group in the pyrimidine moiety, the following scheme can be used with reference to Huang, Z et al., J. Am. Chem. Soc., 132, pp. 2120-2121 (2020).

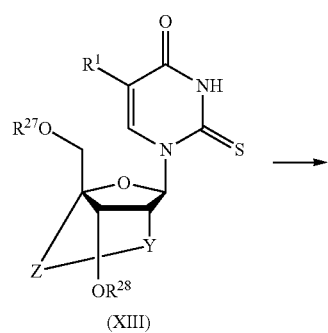

wherein Y, Z, $R^1$, $R^{27}$ and $R^{28}$ are as defined above, and $R^{30}$ is a $C_{1-6}$ alkyl group.

As the nucleic acid compound (XIII), one in which at least the 5'-position hydroxyl group is protected is preferable since unprotected 5'-position hydroxyl group may be alkylated during S-alkylation. A method of directly converting the functional group of the 2-position thiocarbonyl group of nucleic acid compound (XIII) to a selenocarbonyl group by using a Woollins reagent is possible. However, since the 4-position carbonyl group may be selenocarbonylated, it is preferable to obtain nucleic acid compound (XIV) by selectively alkylating the 2-position thiocarbonyl group that is adjacent to two nitrogen atoms and is negatively polarized more easily than the oxygen atom of the 4-position carbonyl group. Such alkylation facilitates elimination of the 2-position sulfur atom. Then, nucleic acid compound (XV) can be obtained by reacting nucleic acid compound (XIV) with selenium together with a relatively weak reducing agent such as sodium borohydride and the like.

Furthermore, since the selenocarbonyl group is unstable and has high reactivity as compared to the thiocarbonyl group, it is preferably protected as shown in the following formula when a phosphate group is introduced at the 3'-position. Of course, the 2-position thiocarbonyl may be protected. In the present disclosure, a phosphorous acid group is also included in the phosphate group for convenience.

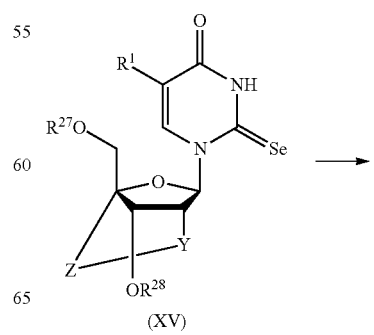

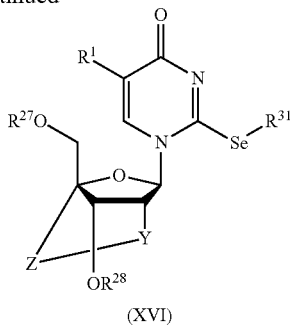

(XVI)

wherein Y, Z, $R^1$, $R^{27}$ and $R^{28}$ are as defined above, and $R^{31}$ is a $C_{1-6}$ alkyl group or a 2-cyanoethyl group.

Furthermore, a nucleic acid compound having a phosphoramidite group introduced into the 3'-position hydroxyl group can be used as a monomer for automatic synthesis of oligonucleotides. Examples of the phosphoramidite group include —P(OCH$_2$CH$_2$CN) (N(iPr)$_2$) group, and —P(OCH$_2$CN) (N(iPr)$_2$) group wherein iPr is an isopropyl group. Using a 2-cyanoethyl group (—CH$_2$CH$_2$CN group) as a protecting group of the 2-position thiocarbonyl group or the 2-position selenocarbonyl group, it can be simultaneously deprotected when the protecting group of the phosphate group is removed during automatic synthesis of oligonucleotides.

In synthesizing the nucleic acid compound of the present invention, the functional groups may be selectively protected or deprotected, or the protecting group may be exchanged in a timely manner by methods known to those skilled in the art.

The oligonucleotide according to the present invention can be synthesized, for example, by general automatic synthesis of nucleic acids except that the above-mentioned nucleic acid compound having a phosphoramidite introduced at the 3'-position is used as a monomer. The group that binds the 5'-position and 3'-position of the nucleic acid residue is not particularly limited as long as it is used in oligonucleotides such as a general phosphate group, a phosphite group, a thiophosphate group and the like.

When the oligonucleotide according to the present invention is used in an antisense method, at least one or more thymidine or uridine in the sequence of the oligonucleotide according to the present invention is introduced by the above-mentioned nucleic acid compound according to the present invention, and thus, formation of T-G or U-G non-Watson-Crick base pairs is suppressed, and the occurrence of side effects due to off-target effects is suppressed. When used in the antisense method, the base sequence of oligonucleotide is preferably complementary to the target mRNA. However, one or more of thymidine and uridine of the oligonucleotide is introduced with the nucleic acid compound according to the present invention, that is, the 2-position carbonyl group of thymine or uracil is functionally converted with sulfur or selenium, and the 2'-position and 4'-position are bridged.

The base length of the oligonucleotide according to the present invention is preferably not less than 7 nt and not more than 30 nt. When the base length is not less than 7 nt, the binding affinity and specificity to the target mRNA can be sufficiently ensured. On the other hand, when the base length is not more than 30 nt, the antigenicity is sufficiently suppressed and synthesis is facilitated. The base length is preferably not less than 10 nt, more preferably not less than 12 nt, and preferably not more than 25 nt and preferably not more than 20 nt. The number of oligonucleic acids with a base length of 17 nt is $4^{17}=1.7\times10^{10}$ and exceeds $2\times3\times10^9$ which is the total number of bases in the human genome. Accordingly, it is also possible to set the base length to not less than 17 nt to improve specificity.

In the oligonucleotide, the nucleic acid residues at the both terminal sites are preferably 2',4'-bridged nucleic acids. Since the nucleic acids at the both terminal sites are 2',4'-bridged, the oligonucleotide do not easily receive attacks by various nucleases in vivo and can be present in the living body for a long time after administration to the living body. In addition, since the structure is stabilized by 2',4'-bridging, a double strand is easily formed with the target mRNA. The length of the both terminal sites of the 2',4'-bridged nucleic acid may be appropriately adjusted. For example, the length is each independently not less than 1 nt and not more than 5 nt from the both terminals. The number of modified bases at the both terminal sites varies depending on the 2',4'-bridged nucleic acid residues at the respective both terminal sites and is preferably not more than 5 nt or not more than 4 nt, more preferably not more than 3 nt, further more preferably 1 nt or 2 nt.

In the present invention, thymidine or uridine in one or more 2',4'-bridged nucleic acid residues at the above-mentioned both terminal sites is preferably introduced with the nucleic acid compound according to the present invention.

The oligonucleotide according to the present invention has one or more 2',4'-non-bridged nucleic acid residues between both terminal sites composed of 2',4'-bridged nucleic acid residues. Hereinafter, in the present disclosure, the parts other than the above-mentioned both terminal sites are sometimes referred to as a "middle part". The 2',4'-non-bridged nucleic acid residue in the middle part may be RNA, DNA, a nucleic acid derivative, or a combination of two or more of these as long as bridging is absent between the 2' position and the 4' position. Examples of the nucleic acid derivative include 2'-$C_{1-6}$ alkylcarbonyloxynucleic acids such as 2'-halogenonucleic acid, 2'-acetoxynucleic acid and the like, 2'-$C_{1-6}$ alkyloxynucleic acids such as 2'-methoxynucleic acid and the like, 2'-tri$C_{1-6}$ alkylsilyloxynucleic acids such as 2'-trimethylsilyloxynucleic acid and the like, and the like. It is preferable that all the nucleic acids in the above-mentioned middle part be DNAs. When all the nucleic acids in the middle part are DNAs, an RNA-DNA double strand is formed to the target mRNA, the double strand becomes a substrate for RNAseH, and the target mRNA is cleaved. From the aspect of the substrate of RNAseH, the length of the above-mentioned middle part is preferably not less than 4 nt, more preferably not less than 5 nt, and still more preferably not less than 6 nt. On the other hand, the length of the above-mentioned middle part is preferably not more than 10 nt from the aspect of antigenicity.

The oligonucleotide of the present invention can be formulated as a parenteral preparation or a liposome preparation by blending with, for example, adjuvants generally used in the technical field of preparation formulation of medicaments such as excipient, binder, preservative, oxidation stabilizer, disintegrant, lubricant, corrigent and the like. In addition, a topical preparation such as liquid, cream, ointment and the like can be formulated by blending with, for example, a pharmaceutical carrier generally used in the pertinent technical field.

The oligonucleotide of the present invention can be administered to human and animals other than human. The dose may be appropriately adjusted depending on the patient's age, sex, body weight, condition, the kind of disease, severity, prophylactic or therapeutic use, and the like. For example, a dose per administration and per kg body weight for adult human is not less than 0.01 μg and not more than 100 g. The dose is preferably not less than 0.1 μg or not less than 1.0 μg, more preferably not less than 10 μg or not less than 100 μg, further preferably not less than 1 mg, and preferably not more than 10 g or not more than 1.0 g, more preferably not more than 100 mg or not more than 10 mg, further more preferably not more than 5 mg. The frequency of administration may be appropriately adjusted between once per month and about not more than 3 times per day.

This application claims the benefit of priority right based on a patent application No. 2017-30490 filed in Japan (filing date: Feb. 21, 2017). The contents of Japanese patent application No. 2017-30490 filed on Feb. 21, 2017 are incorporated in full herein for reference.

EXAMPLES

The present invention is more specifically described by way of Examples. However, the present invention is not limited by the following Examples, and appropriate modifications may be made within the range compatible to the above-mentioned and the later-mentioned gist. All of such modifications are encompassed in the technical scope of the present invention.

Example 1: Synthesis of scpBNA-S²T

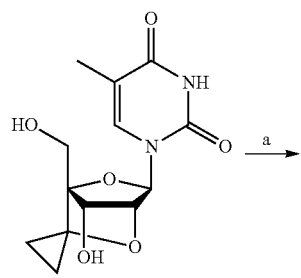

1

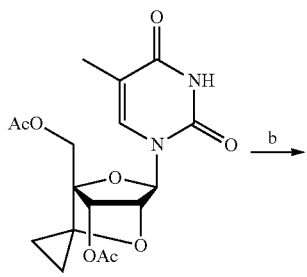

2

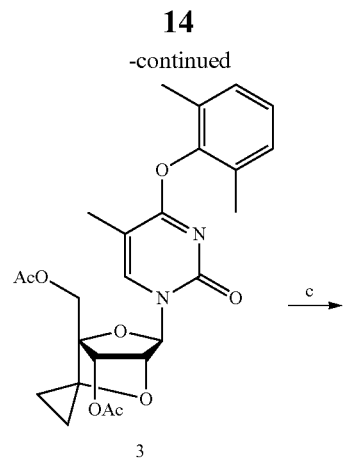

3

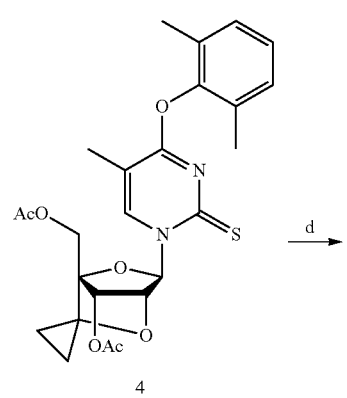

4

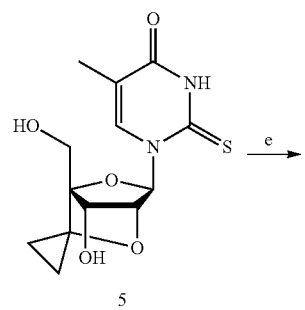

5

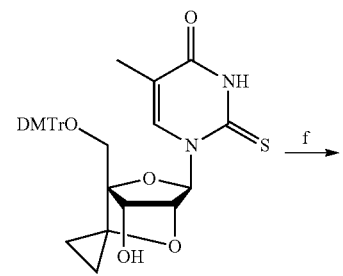

6

-continued

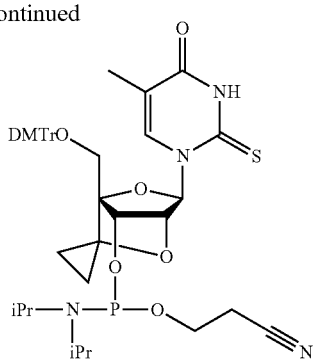

(1) Synthesis of Compound 2

Compound 1 (32 mg, 0.11 mmol) was azeotropically distilled with dehydration with anhydrous pyridine, anhydrous pyridine (1.1 mL), 4-dimethylaminopyridine (7 mg, 0.06 mmol) and acetic anhydride (30.5 μL, 0.32 mmol) were successively added under a nitrogen stream, and the mixture was stirred at room temperature for 40 min. After completion of the reaction, water was added and the mixture was extracted with ethyl acetate. The extract was washed with water, the solvent was evaporated under reduced pressure, and the residue was azeotropically distilled with toluene. The obtained residue was purified by silica gel column chromatography ($SiO_2$, ethyl acetate:hexane=2:1) to give compound 2 (yield amount: 40 mg, yield ratio: quantitative) as a white solid.

$^1$H NMR (300 MHz, $CDCl_3$) δ 0.77-1.02 (m, 4H), 1.96 (d, J=1.4 Hz, 3H), 2.14 (s, 3H), 2.18 (s, 3H), 4.03 (d, J=12.4 Hz, 1H), 4.26 (d, J=12.9 Hz, 1H), 4.69 (s, 1H), 4.99 (s, 1H), 5.80 (s, 1H), 7.51 (d, J=1.4 Hz, 1H), 8.93 (s, 1H)

$^{13}$C NMR (76 MHz, $CDCl_3$) δ 5.4, 9.7, 13.1, 20.8, 20.9, 58.1, 68.3, 72.5, 78.1, 85.9, 87.1, 110.8, 134.1, 149.8, 163.5, 170.1, 170.1

IR(KBr): 3022, 2840, 1746, 1704, 1239, 1212, 1052 $cm^{-1}$
$[α]_D^{23}$ +28.40 (c1.00, $CHCl_3$)
HRMS(MALDI) Calcd. for $C_{17}H_{20}N_2O_8Na$ $[M+Na]^+$: 403.1112, Found: 403.1113.

(2) Synthesis of Compound 3

Compound 2 (270 mg, 0.71 mmol) was dried under reduced pressure in the presence of phosphorus pentaoxide and dissolved in anhydrous acetonitrile (7.1 mL). Under a nitrogen stream, 2,4,6-triisopropylbenzenesulfonylchloride (279 mg, 0.92 mmol) and dried potassium carbonate (490 mg, 3.54 mmol) were added, and the mixture was stirred at 60° C. for 2.5 hr. After disappearance of the starting materials, the reaction solution was allowed to cool to room temperature, 2,6-dimethylphenol (121 mg, 0.99 mmol) and 1,4-diazabicyclo-2,2,2-octane (24 mg, 0.21 mmol) were added and the mixture was stirred at 50° C. for 1 hr. The reaction solution was added dropwise to a saturated aqueous ammonium chloride solution cooled to 0° C., and the mixture was extracted with ethyl acetate. The organic phase was washed with water and saturated brine, dried over anhydrous sodium sulfate and the solvent was evaporated under reduced pressure. The obtained residue was purified by silica gel column chromatography ($SiO_2$, ethyl acetate: hexane=1:1) to give compound 3 (yield amount: 337 mg, yield ratio: quantitative) as a white solid.

$^1$H NMR (300 MHz, $CDCl_3$) δ 0.77-1.01 (m, 4H) (s, 3H), 2.13 (s, 3H), 2.15 (s, 3H), 2.21 (s, 6H), 4.03 (d, J=12.4 Hz, 1H), 4.30 (d, J=12.9 Hz, 1H), 4.77 (s, 1H), 5.03 (s, 1H), 5.86 (s, 1H), 7.05 (s, 3H), 7.82 (d, J=0.9 Hz, 1H)

$^{13}$C NMR (76 MHz, $CDCl_3$) δ 5.3, 9.6, 13.1, 16.6, 16.7, 20.8, 20.9, 58.2, 68.2, 72.3, 77.9, 85.9, 87.9, 104.2, 126.0, 128.8, 139.7, 149.4, 155.2, 170.1, 170.2

IR(KBr): 2927, 1748, 1669, 1537, 1218, 1048 $cm^{-1}$
$[α]_D^{24}$ +86.19 (c1.00, $CDCl_3$)
HRMS(MALDI) Calcd. for $C_{25}H_{28}N_2O_8Na$ $[M+Na]^+$: 507.1738, Found: 507.1740.

(3) Synthesis of Compound 4

Under a nitrogen stream, to a solution (8.7 mL) of compound 3 (422 mg, 0.87 mmol) in anhydrous toluene was added a Lawesson reagent (352 mg, 0.87 mmol) and the mixture was heated under reflux for 1 hr. After completion of the reaction, and the mixture was cooled to 0° C., and the precipitate was filtered. The filtrate was concentrated under reduced pressure and the obtained compound 4 (656 mg, crude) as a yellow solid was immediately used for the next reaction without further purification.

(4) Synthesis of Compound 5

Compound 4 (656 mg, crude) was azeotropically distilled with dehydration with anhydrous toluene, anhydrous acetonitrile (8.7 mL), dried potassium carbonate (722 mg, 5.23 mmol) and syn-o-nitrobenzaldoxime (434 mg, 2.61 mmol) were successively added under a nitrogen stream, 50° C. for 17.5 hr was stirred. Thereafter, methanol (8.7 mL) was added and the mixture was stirred at 50° C. for 20 min. After completion of the reaction, the mixture was cooled to room temperature and the precipitate was filtered. The filtrate was concentrated under reduced pressure, and the obtained residue was purified by silica gel column chromatography ($SiO_2$, chloroform:methanol=12:1) to give compound 5 (yield amount in two steps: 173 mg, yield ratio: 64%) as a brown solid.

$^1$H NMR (300 MHz, $CD_3OD$) δ0.73-0.93 (m, 4H), 1.94 (d, J=1.4 Hz, 3H), 3.57 (d, J=12.9 Hz, 1H), 3.74 (d, J=12.4 Hz, 1H), 4.18 (s, 1H), 4.63 (s, 1H), 6.16 (s, 1H) 7.98 (d, J=1.4 Hz, 1H)

$^{13}$C NMR (76 MHz, $CD_3OD$) δ5.0, 9.9, 12.9, 56.6, 68.6, 71.7, 80.6, 90.6, 91.3, 116.0, 138.2, 163.3, 175.5

IR(KBr): 3076, 2942, 1681, 1496, 1273, 1040 $cm^{-1}$
$[α]_D^{25}$ −9.5 (c1.00, MeOH)
HRMS(MALDI) Calcd. for $C_{13}H_{16}N_2O_5NaS$ $[M+Na]^+$: 335.0672, Found: 335.0656.

(5) Synthesis of Compound 6

Compound 5 (165 mg, 0.53 mmol) was azeotropically distilled with dehydration with anhydrous pyridine, under a nitrogen stream, anhydrous pyridine (10.6 mL) and 4,4'-dimethoxytritylchloride (268 mg, 0.79 mmol) were added, and the mixture was stirred at room temperature for 4.5 hr. After completion of the reaction, water was added, and the mixture was extracted with ethyl acetate. The extract was washed with water, the solvent was evaporated under reduced pressure, and the residue was azeotropically distilled with toluene. The obtained residue was purified by silica gel column chromatography ($SiO_2$, containing 0.5% triethylamine, ethyl acetate:hexane=1:1) to give compound 6 (yield amount: 311 mg, yield ratio: 96%) as a white solid.

$^{1}$H NMR (300 MHz, CDCl$_{3}$) δ0.51-0.55 (m, 1H), 0.71-0.74 (m, 1H), 0.89-0.98 (m, 2H), 1.69 (d, J=0.9 Hz, 3H), 2.26 (d, J=9.2 Hz, 1H), 3.18 (d, J=11.0 Hz, 1H), 3.34 (d, J=10.6 Hz, 1H), 3.79 (s, 6H), 4.32 (d, J=9.6 Hz, 1H), 4.77 (s, 1H), 6.23 (s, 1H), 6.85 (d, J=8.3 Hz, 4H), 7.24-7.36 (m, 7H), 7.43-7.46 (m, 2H), 7.84 (d, J=1.4 Hz, 1H), 9.79 (s, 1H)

$^{13}$C NMR (76 MHz, CDCl$_{3}$) δ5.4, 9.7, 12.9, 55.4, 57.7, 67.8, 72.7, 79.2, 87.2, 88.8, 90.1, 113.5, 116.2, 127.3, 128.2, 128.2, 130.2, 130.2, 135.1, 135.3, 136.0, 14 4.3, 158.9, 160.7, 173.6

IR(KBr): 3432, 2956, 1681, 1508, 1253, 1177, 1046, 833, 766 cm$^{-1}$ $[α]_{D}^{25}$ −38.0 (c1.00, CDCl$_{3}$)

HRMS(MALDI) Calcd. For C$_{34}$H$_{34}$N$_{2}$O$_{7}$NaS [M+Na]$^{+}$: 637.1979, Found: 637.1972.

(6) Synthesis of Compound 7

Compound 6 (41 mg, 0.07 mmol) was azeotropically distilled with dehydration with anhydrous toluene, anhydrous acetonitrile (0.7 mL), N,N-diisopropylethylamine (34.5 μL, 0.20 mmol) and 2-cyanoethyl-N,N-diisopropylphosphorochloridate (22.5 μL, 0.10 mmol) were successively added under a nitrogen stream, and the mixture was stirred at room temperature for 4 hr. The solvent was evaporated under reduced pressure, and the obtained residue was purified by silica gel column chromatography (SiO$_{2}$, containing 0.5% triethylamine, ethyl acetate:hexane=1:1) to give compound 7 (yield amount: 43 mg, yield ratio: 78%) as a white solid.

$^{31}$P NMR (121.7 MHz, CDCl$_{3}$) δ148.7, 149.2

HRMS(MALDI) Calcd. for C$_{43}$H$_{51}$N$_{4}$O$_{8}$NaPS [M+Na]$^{+}$: 837.3057, Found: 837.3055.

Example 2: Synthesis of scpBNA-Se$^{2}$T

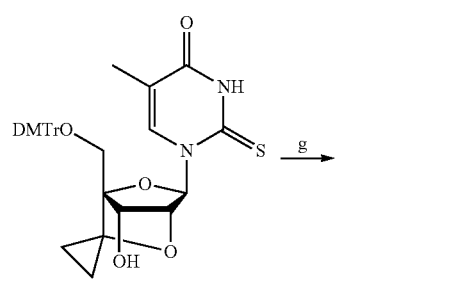

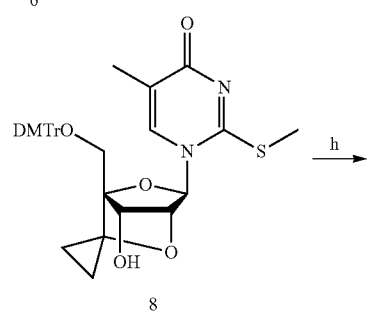

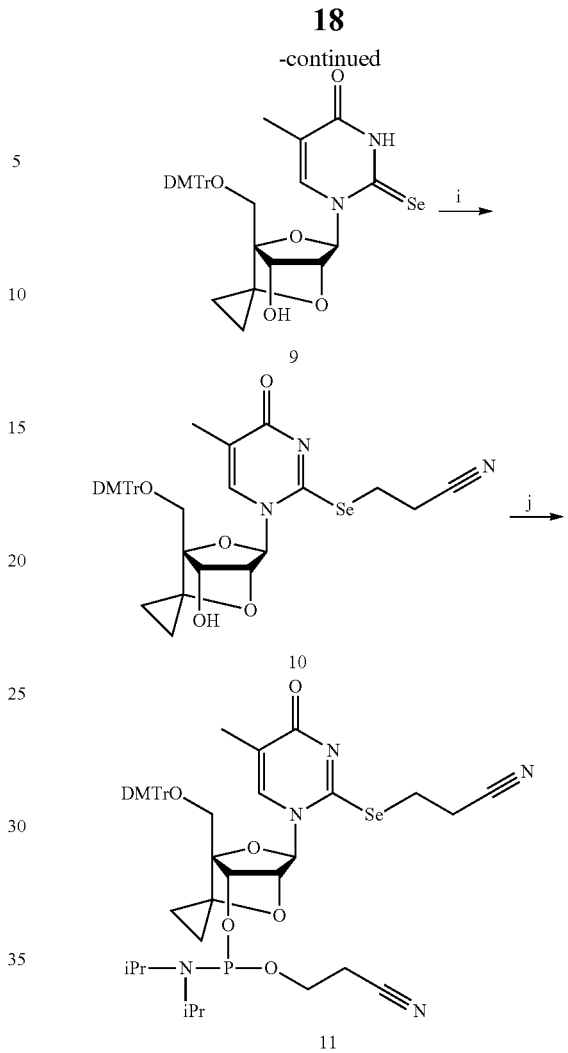

(1) Synthesis of Compound 8

Under a nitrogen stream, to a solution (6.7 mL) of compound 6 (412 mg, 0.67 mmol) in anhydrous DMF were added iodomethane (420 μL, 6.75 mmol) and 1,8-diazabicyclo[5.4.0]-7-undecene (150 μL, 1.00 mmol), and the mixture was stirred at 0° C. for 1 hr. After completion of the reaction, an excess amount of water was added, and the precipitate was collected by filtration. The obtained residue was purified by silica gel column chromatography (SiO$_{2}$, ethyl acetate:methanol=13:1) to give compound 8 (yield amount: 336 mg, yield ratio: 80%) as a pale-yellow solid.

$^{1}$H NMR (300 MHz, CDCl$_{3}$) δ0.53-0.63 (m, 1H), 0.77-0.91 (m, 3H), 1.78 (d, J=0.9 Hz, 3H), 2.61 (s, 3H), 3.09 (d, J=8.1 Hz, 1H), 3.20 (d, J=10.8 Hz, 1H), 3.40 (d, J=11.0 Hz, 1H), 3.78 (s, 6H), 4.38 (d, J=7.6 Hz, 1H), 4.44 (s, 1H), 5.80 (s, 1H), 6.82-6.85 (m, 4H), 7.21-7.35 (m, 7H), 7.44-7.47 (m, 2H), 7.82 (d, J=1.2 Hz, 1H)

$^{13}$C NMR (76 MHz, CDCl$_{3}$) δ 5.5, 9.8, 14.2, 14.7, 55.4, 57.9, 68.3, 72.2, 80.1, 87.1, 88.3, 113.5, 118.8, 127.3, 128.1, 128.2, 130.1, 130.2, 133.7, 135.1, 135.3, 144.3, 158.8, 1 60.2, 169.5

IR(KBr): 2933, 1640, 1609, 1509, 1486, 1254, 1177, 1046, 755 cm$^{-1}$ $[α]_{D}^{21}$ −25.32 (c1.00, CHCl$_{3}$)

HRMS(MALDI) Calcd. for $C_{35}H_{36}N_2O_7NaS$ [M+Na]$^+$: 651.2135, Found: 651.2134.

(2) Synthesis of Compound 9

Under a nitrogen stream, to anhydrous ethanol (4.5 mL) were added selenium (107 mg, 1.36 mmol) and sodium borohydride (62 mg, 1.64 mmol), and the mixture was stirred at 0° C. for 30 min until a transparent solution was obtained. An ethanol solution of the produced NaSeH was added to compound 8 (261 mg, 0.42 mmol), which was azeotropically distilled with dehydration in advance with anhydrous toluene, under a nitrogen stream at 0° C. while avoiding contact with air. After stirring for 3 days at room temperature, water was added, the mixture was filtered through celite and the filtrate was extracted with ethyl acetate. The extract was washed with water and saturated brine, dried over anhydrous sodium sulfate and the solvent was evaporated under reduced pressure. The obtained residue was purified by silica gel column chromatography (SiO$_2$, ethyl acetate:hexane=1:1) to give compound 9 (yield amount: 230 mg, yield ratio: 84%) as a pale-yellow solid.

$^1$H NMR (300 MHz, CDCl$_3$) δ0.49-0.57 (m, 1H), 0.68-0.76 (m, 1H), 0.86-1.04 (m, 2H), 1.63 (d, J=1.0 Hz, 3H), 2.09 (d, J=10.0 Hz, 1H), 3.19 (d, J=10.8 Hz, 1H), 3.33 (d, J=10.8 Hz, 1H), 3.80 (s, 6H), 4.33 (d, J=8.9 Hz, 1H), 4.88 (s, 1H), 6.30 (s, 1H), 6.84-6.87 (m, 4H), 7.23-7.46 (m, 9H), 7.88 (d, J=1.2 Hz, 1H), 9.91 (s, 1H)

$^{13}$C NMR (76 MHz, CDCl$_3$) δ 5.4, 9.7, 13.1, 55.4, 57.6, 67.8, 72.6, 79.6, 87.2, 89.1, 92.2, 113.5, 118.0, 127.4, 128.1, 128.2, 130.2, 130.2, 135.1, 135.2, 136.2, 144.3, 158.9, 160.0, 173.5

IR(KBr): 2936, 1682, 1509, 1255, 1178, 1053, 1038, 757, 606 cm$^{-1}$ $[\alpha]_D^{20}$ −52.56 (c1.00, CHCl$_3$)

HRMS(MALDI) Calcd. for $C_{34}H_{34}N_2O_7NaSe$ [M+Na]$^+$: 685.1423, Found: 685.1429.

(3) Synthesis of Compound 10

Under a nitrogen stream, to a solution (1.5 mL) of compound 9 (98 mg, 0.15 mmol) and 3-iodopropionitrile (200 µL, 2.25 mmol) in anhydrous dichloromethane was added dropwise N,N-diisopropylethylamine (380 µL, 2.22 mmol) at 0° C. After stirring at 0° C. for 40 min, 3-iodopropionitrile and N,N-diisopropylethylamine were further added and the mixture was stirred until the starting materials disappeared. After disappearance of the starting materials, water was added, and the mixture was extracted with ethyl acetate. The extract was washed with water and saturated brine, dried over anhydrous sodium sulfate and the solvent was evaporated under reduced pressure. The obtained residue was purified by silica gel column chromatography (SiO$_2$, ethyl acetate:methanol=1:0→12:1) to give compound 10 (yield: 99 mg, yield: 94%) as a pale-yellow solid.

$^1$H NMR (300 MHz, CDCl$_3$) δ0.54-0.58 (m, 1H), 0.77-0.96 (m, 3H), 1.78 (d, J=1.0 Hz, 3H), 2.51 (d, J=8.9 Hz, 1H), 3.01-3.06 (m, 2H), 3.21 (d, J=11.0 Hz, 1H), 3.37 (d, J=11.0 Hz, 1H), 3.42-3.55 (m, 2H), 3.79 (s, 6H), 4.39 (d, J=8.9 Hz, 1H), 4.42 (s, 1H), 5.69 (s, 1H), 6.82-6.87 (m, 4H), 7.25-7.46 (m, 9H), 7.85 (d, J=1.2 Hz, 1H)

$^{13}$C NMR (76 MHz, CDCl$_3$) δ 5.5, 9.8, 14.2, 18.9, 23.8, 55.4, 57.7, 68.3, 72.2, 80.3, 87.2, 88.5, 89.4, 113.5, 118.8, 119.9, 127.3, 128.1, 128.3, 130.1, 130.2, 134.2, 135.1, 135.2, 144.3, 154.8, 158.9, 168.9

IR(KBr): 3006, 2951, 1634, 1609, 1508, 1485, 1253, 1177, 1053, 1039, 834, 752, 581 cm$^{-1}$ $[\alpha]_D^{20}$ −38.08 (c1.00, CHCl$_3$)

HRMS(MALDI) Calcd. for $C_{37}H_{37}N_3O_7NaSe$ [M+Na]$^+$: 738.1689, Found: 738.1706.

(4) Synthesis of Compound 11

Compound 10 (139 mg, 0.19 mmol) was azeotropically distilled with dehydration with anhydrous toluene, anhydrous acetonitrile (2.0 mL), N,N-diisopropylethylamine (100 µL, 0.58 mmol) and 2-cyanoethyl-N,N-diisopropylphosphorochloridate (65 µL, 0.29 mmol) were successively added under a nitrogen stream, and the mixture was stirred at room temperature for 2 hr. The solvent was evaporated under reduced pressure, and the obtained residue was purified by diol silica gel column chromatography (DIOL-SiO$_2$, ethyl acetate:hexane=1:2→1:10) to give compound 11 (yield amount: 144 mg, yield ratio: 81%) as a white solid.

$^{31}$P NMR (121.7 MHz, CDCl$_3$) δ149.1, 149.5

HRMS(MALDI) Calcd. for $C_{46}H_{54}N_5O_8NaPSe$ [M+Na]$^+$:938.2767, Found: 938.2777.

Example 3: Synthesis of Oligonucleotide

Oligonucleotides used in the following Experimental Examples were synthesized under the following conditions. A 0.1M anhydrous acetonitrile solution of the amidite blocks synthesized in Examples 1 and 2 (compounds 7 and 11) and commercially available dG (iBu), dC (Bz) and T phosphoramidite was prepared, and oligonucleotides were synthesized on a 0.2 µmol scale, trityl-on condition using GeneDesign nS-8 Oligonucleotides Synthesizer. Activator 42 (0.25 M acetonitrile solution) was used as the activator, and the condensation time was 8 min for the amidite block and 32 sec for the natural amidite blocks. The oxidizing agent used was tert-butyl hydroperoxide/acetonitrile/water (7:60:3), and the oxidation time was 10 min. Other operations followed general phosphoramidite method. After completion of the synthesis, oligonucleotides were treated with 28% aqueous ammonia solution at room temperature for 1.5 hr, cut out from the column carrier and subsequently stood at 55° C. for 3 hr to deprotect the base part and the phosphoric acid diester part. Successively, the oligonucleotides were purified by a simple reversed-phase column (Waters Sep-Pak (registered trade mark) Plus C18 Environmental Cartridges), and further purified by reversed-phase HPLC.

Confirmation of the structure and quantification of the obtained oligonucleotide were performed under the following conditions. On an anchor chip on which a matrix (10 mg/mL 3-hydroxypicolinic acid aqueous solution: 1 mg/mL diammonium citrate aqueous solution=1:1, 1 µL) had been dried was placed each oligonucleotide aqueous solution (50 µM, 1 µL) and the chip was dried again, and the molecular weight of oligonucleotide was confirmed by MALDI-TOF MS. The molecular weight was measured in the negative reflector mode and oligothymidylic acid (7 mer, 15 mer and 23 mer) was used as an external standard. The oligonucleotide was quantified by measuring the ultraviolet absorption at 254 nm using an absorbance meter.

Experimental Example 1: Double Strand Formability Test for Complementary Strand RNA and Mismatch Sequence RNA The synthesis of ssRNA having the sequence 5'-r(AGCAAAYAACGC)-3' was committed to GeneDesign, Inc. An oligonucleotide (5'-d(GCGTTXTTTGCT)-3') containing the ssRNA (5'-r(AGCAAAYAACGC)-3') and 2',4'- bridged nucleic acids synthesized in Examples 1 and 2 and sodium chloride was added to phosphate buffer (10 mM, pH 7.2, 130 μL) at final concentrations of 4 μM and 100 mM, mixed, bathed in boiling water and then slowly cooled to room temperature. Thereafter, the sample was cooled to 50° C. under a nitrogen stream, and the temperature was raised to 90° C. at 0.5° C./min during which the absorbance at 260 nm was measured at 0.5° C. intervals. Absorbance against temperature was plotted, and $T_m$ value was calculated by the midline method. The measurement was performed three times, and the mean of $T_m$ values was calculated. The results are shown in Table 1.

TABLE 1

| oligonucleotide | | $T_m$ ($\Delta T_m = T_m$[mismatch] − $T_m$[match]) (° C.) | | | |
|---|---|---|---|---|---|
| No. | X | Y = A | Y = G | Y = C | Y = U |
| Comp. Ex. 1 | scpBNA-T | 53 | 47 (−6) | 35 (−18) | 38 (−15) |
| Ex. 1 | scpBNA-S$^2$T | 54 | 42 (−12) | 36 (−18) | 42 (−12) |
| Ex. 2 | scpBNA-Se$^2$T | 52 | 40 (−12) | 34 (−18) | 41 (−11) |

As shown in the results of Table 1, when the 2-position carbonyl group of thymine was converted to a thiocarbonyl group or a selenocarbonyl group in addition to the 2',4'-bridge (Examples 1, 2), the $T_m$ value of Watson-Crick base pair between T-A did not change but the $T_m$ value of the wobble base pair between T-G could be clearly reduced as compared with when only the 2',4'-position bridge of thymidine was formed (Comparative Example 1). Thus, it was demonstrated that introduction of the nucleic acid according to the present invention into an oligonucleotide can suppress formation of a mismatch base pair between T-G and reduce off-target.

Experimental Example 2: Double Strand Formability Test for Complementary Strand DNA and Mismatch Sequence RNA The synthesis of ssDNA having the same base sequence as the ssRNA used in the above-mentioned Experimental Example 1 was committed to GeneDesign, Inc. In the same manner as in the above-mentioned Experimental Example 1 except that the ssDNA was used instead of ssRNA, $T_m$ values with the oligonucleotides shown in Table 2 were determined. The results are shown in Table 2.

TABLE 2

| oligonucleotide | | $T_m$ ($\Delta T_m = T_m$[mismatch] − $T_m$[match]) (° C.) | | | |
|---|---|---|---|---|---|
| No. | X | Y = A | Y = G | Y = C | Y = U |
| Comp. Ex. 1 | scpBNA-T | 53 | 43 (−10) | 38 (−15) | 40 (−13) |
| Ex. 1 | scpBNA-S$^2$T | 54 | 40 (−14) | 34 (−20) | 43 (−11) |
| Ex. 2 | scpBNA-Se$^2$T | 53 | 37 (−16) | 33 (−20) | 40 (−13) |

As shown in the results of Table 2, it was demonstrated that introduction of the nucleic acid according to the present invention into an oligonucleotide can suppress formation of a mismatch base pair between T-G and reduce off-target also in DNA.

Experimental Example 3: Gene Expression-Suppressing Effect in Mouse

GR (Glucocortiocoid Receptor) is one kind of steroid receptors and works as a receptor for the steroid hormone hydrocortisone. It also undergoes nuclear translocation in a ligand-dependent manner and also works as a transcription factor. Therefore, Posi12 (Nucleic Acid Ther., 2012, 22, 5, 344-359) was selected as an antisense oligonucleic acid targeting same, and the synthesis of Posi12 derivatives was committed to Gene Design, Inc. In Table 3, "(L)" indicates presence of a structure in which the 4'-position and the 2'-position are bridged by —CH$_2$—O—, "^" indicates that the 5'-position and the 3'-position are bonded by a thiophosphate group, "5" indicates 5-methylcytidine, "scpBNA" indicates presence of a structure in which the 4'-position and the 2'-position are bridged by -cyclopropylmethylene-O—, "S$^2$T" indicates that the 2-position of thymine is =S, "AmNA" indicates presence of a structure in which the 4'-position and the 2'-position are bridged by —C(=O)—N(—CH$_3$)—, and small letters indicate DNA.

TABLE 3

| Posi12-LNA-T | G(L)^T(L)^5(L)^t^c^t^t^t^a^c^c^T(L)^G(L)^G(L) |
|---|---|
| Posi12-scpBNA-T | G(L)^T(scpBNA-T)^5(L)^t^c^t^t^t^a^c^c^T(scpBNA-T)^G(L)^G(L) |
| Posi12-scpBNA-S$^2$T | G(L)^T(scp-BNA-S$^2$T)^5(L)^t^c^t^t^t^a^c^c^T(scp-BNA-S$^2$T)^G(L)^G(L) |
| Posi12-AmNA-T | G(L)^T(AmNA-T)^5(L)^t^c^t^t^t^a^c^c^T(AmNA-T)^G(L)^G(L) |

Each antisense oligonucleic acid was dissolved in physiological saline (manufactured by Otsuka Pharmaceutical Co., Ltd.) to give a 2 mg/mL solution, and the solution was cryopreserved at −30° C. until used in experiments.

Five-week-old male C57BL/6NCrl mice (Nihon Charles River Co., Ltd.) were quarantined and acclimated for 1 week. The mice were optionally divided into 5 groups (4 mice per group), and physiological saline (manufactured by Otsuka Pharmaceutical Co., Ltd.) or each antisense oligonucleic acid solution was administered once at a dose of 20 mg/kg body weight from the tail vein. On the fourth day (96 hours later), the mice were anesthetized by inhalation of 2.0 to 4.0% isoflurane (manufactured by DS Pharma Animal Health), and blood was collected from the abdominal portion of posterior vena cava as much as possible. Since two in the Posi12-LNA-T administration group showed a remarkable decrease in the spontaneous movement on day 3, blood samples were collected on day 3. After blood was collected, the mouse was euthanized by freezing, and the liver was removed and the weight was measured. About 100 mg was collected as a sample from a site where no abnormality was found macroscopically in the excised liver. The weight of the collected sample was measured, the sample was frozen in liquid nitrogen and stored in an ultra low temperature freezer. The cryopreserved liver sample was homogenized as much as possible using a homogenizer (Shake Master auto, Bio Medical Science Inc.) and TRIzol reagent (Thermo Fisher Scientific) under ice-cooling and total RNA was extracted. The UV absorption spectrum of the extracted total RNA was measured using Nano Vue or Nano Vue Plus (GE Healthcare), and the purity was calculated from the RNA concentration and O.D.260/O.D.280 ratio. Quantitative PCR was performed on total RNA using One Step SYBR PrimeScript RT-PCR Kit (Takara) and Applied Biosystems 7500 (Life Technologies Japan Ltd), the expression ratio of the target gene in the antisense oligonucleic acid administration group relative to the saline administration group was calculated, and the activity was evaluated. The breeding and experiment in the animal experiment disclosed here were conducted in the animal experiment facility of Safety Laboratory, SHIN NIPPON BIOMEDICAL LABORATORIES, LTD. in accordance with the animal experiment regulations of SHIN NIPPON BIOMEDICAL LABORATORIES, LTD. The results are shown in FIG. 1.

As shown in the results of FIG. 1, it was clarified that the antisense oligonucleic acid (Posi12-scpBNA-S2T) according to the present invention containing a nucleic acid residue in which the 4'-position and the 2'-position are bridged in addition to the modification of the 2-position carbonyl group of thymine can effectively suppress expression of target gene as in other antisense oligonucleic acids.

Experimental Example 4: Gene Expression-Suppressing Effect in Mouse

Posi14 (Nucleic Acid Ther., 2012, 22, 5, 344-359) was selected as an antisense oligonucleic acid targeting mouse GR, and the synthesis of Posi14 derivatives having the sequence shown in Table 4 was committed to Gene Design, Inc.

TABLE 4

| Posi14-LNA-T | A(L)^G(L)^G(L)^t^g^c^t^t^t^g^g^T(L)^5(L)^T(L) |
|---|---|
| Posi14-scpBNA-T | A(L)^G(L)^G(L)^t^g^c^t^t^t^g^g^T(scpBNA-T)^5(L)^T(L) |
| Posi14-scpBNA-S$^2$T | A(L)^G(L)^G(L)^t^g^c^t^t^t^g^g^T(scp-BNA-S$^2$T)^5(L)^T(L) |
| Posi14-AmNA-T | A(L)^G(L)^G(L)^t^g^c^t^t^t^g^g^T(AmNA-T)^5(L)^T(L) |

With regard to each of the obtained antisense oligonucleic acids, the GR gene expression-suppressing activity was measured in the same manner as in the above-mentioned Experimental Example 3. The results are shown in FIG. 2.

Figure 2:
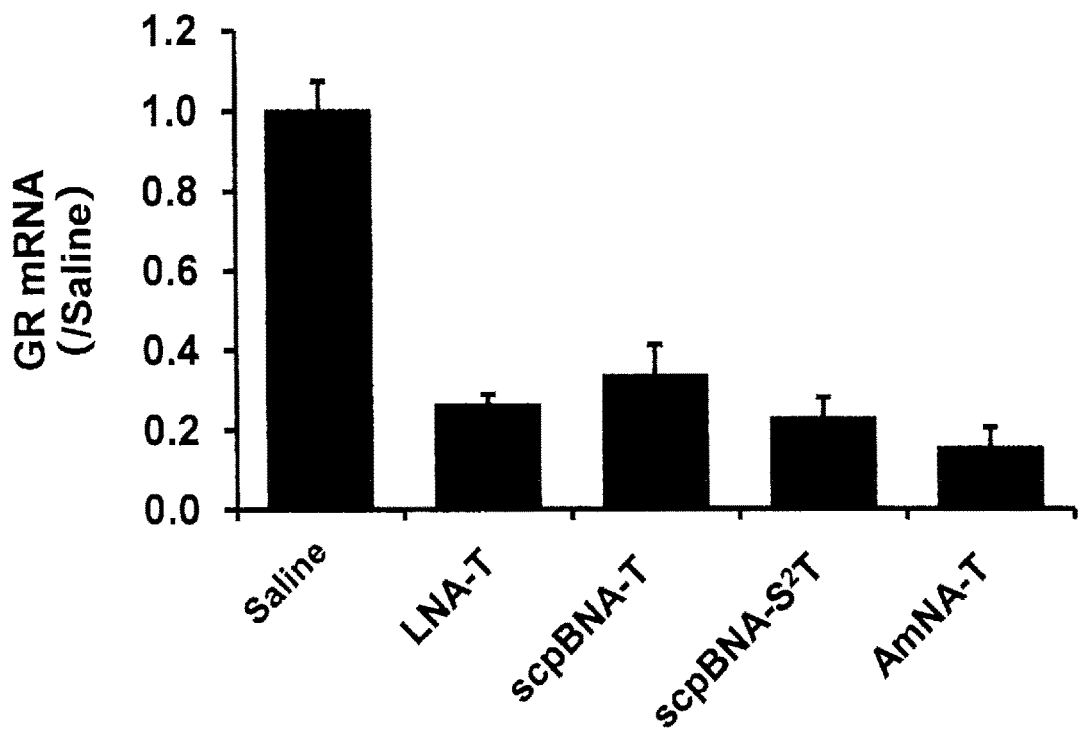
FIG. 2 is a graph showing the results of GR gene expression-suppressing activity evaluated in the Example described later.

As shown in the results of FIG. 2, it was clarified that, even in an antisense oligonucleic acid having other base sequence, the antisense oligonucleic acid (Posi14-scpBNA-S$^2$T) according to the present invention containing a nucleic acid residue in which the 4'-position and the 2'-position are bridged in addition to the modification of the 2-position carbonyl group of thymine can suppress expression of GR gene as in other antisense oligonucleic acids.

Experimental Example 5: Hepatotoxicity Evaluation

12 that induces strong hepatotoxicity was selected, and the synthesis of derivatives of #12 having the sequences shown in Table 5 was committed to Gene Design, Inc.

TABLE 5

| #12-scpBNA-T | G(L) T(scpBNA-T) 5(L) c g c a t g c c T(L) A(L) A(L) |
|---|---|
| #12-scpBNA-S$^2$T | G(L) T(scpBNA-S$^2$T) 5(L) c g c a t g c c T(L) A(L) A(L) |

Five-week-old male C57BL/6NCrl mice (Nihon Charles River Co., Ltd.) were quarantined and acclimated for 1 week. The mice were optionally divided into 3 groups (4 mice per group), and physiological saline (manufactured by Otsuka Pharmaceutical Co., Ltd.) or each antisense oligonucleic acid solution was administered once at a dose of 20 mL/kg body weight from the tail vein. On the fourth day (96 hours later), the mice were anesthetized by inhalation of 2.0 to 4.0% isoflurane (manufactured by DS Pharma Animal Health), and blood was collected from the abdominal portion of posterior vena cava as much as possible. The obtained blood was allowed to stand at room temperature for 20 to 60 min and centrifuged at 1700×g for 5 min to give serum. At the time of blood collection, when the blood volume did not reach the amount necessary for analysis, it was diluted with water for injection and used for the analysis. The concentration of alanine transaminase (ALT) in the obtained serum was measured using an automatic biochemical analyzer ("JCA-BM6070" manufactured by JEOL Ltd.). The results are shown in FIG. 3.

As shown in the results of FIG. 3, it was clarified that the hepatotoxicity of the antisense oligonucleic acid (#12-scpBNA-S$^2$T) according to the present invention containing a nucleic acid residue in which the 4'-position and the 2'-position are bridged in addition to the modification of the 2-position carbonyl group of thymine was reduced. The reason therefor is considered to be that the nucleic acid residue according to the present invention suppressed formation of non-Watson-Crick base pairs, which in turn suppressed non-specific binding with nucleic acids other than the target nucleic acid.

The invention claimed is:

1. An oligonucleotide having one or more nucleic acid residues with a structure represented by the following formula (IX), or a pharmacologically acceptable salt thereof:

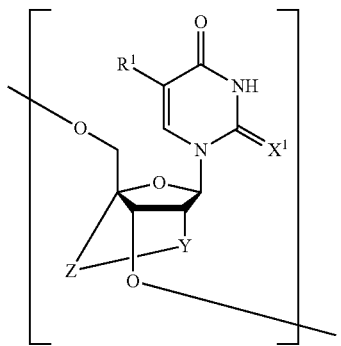
(IX)

wherein $X_1$ is S or Se,

Y is a guanidino group represented by any of the following formulas (III)-(VI), and Z is a single bond or a $C_{1-4}$ alkylene group,

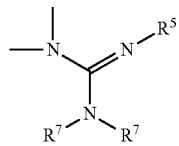
(III)

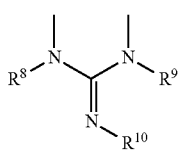
(IV)

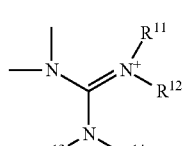
(V)

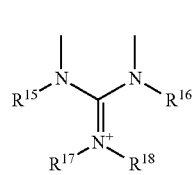
(VI)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, or Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the following formula (VII):

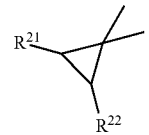
(VII)

wherein $R^{21}$ and $R^{22}$ are each independently H, a $C_{1-6}$ alkyl group, or $R^{21}$ and $R^{22}$ are optionally joined to form a $C_{1-4}$ alkylene group, or Y and Z are joined to form a —C(=O)—O— group or a —C(=O)—N($R^{20}$)— group ($R^{20}$ is H or a $C_{1-6}$ alkyl group), and $R^1$ is H or a $C_{1-6}$ alkyl group.

2. The oligonucleotide according to claim 1, wherein Y is O and Z is a cyclopropyl group represented by the above-mentioned formula (VII), or a pharmacologically acceptable salt thereof.

3. The oligonucleotide according to claim 2, wherein $R^1$ is a methyl group, or a pharmacologically acceptable salt thereof.

4. The oligonucleotide according to claim 1, wherein $R^1$ is a methyl group, or a pharmacologically acceptable salt thereof.

5. A method of reducing side effects of an oligonucleotide, comprising bridging the 2'-position and 4'-position of one or more nucleic acid residues thereof with a —Y—Z— group to form the oligonucleotide according to claim 1: wherein Y is a guanidino group represented by any of the following formulas (III)-(VI), and Z is a single bond or a $C_{1-4}$ alkylene group,

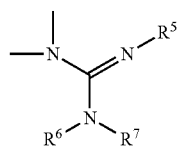
(III)

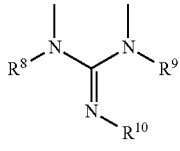
(IV)

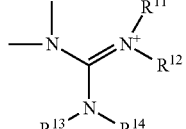
(V)

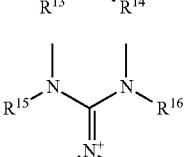
(VI)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, or Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the following formula (VII):

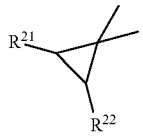
(VII)

wherein $R^{21}$ and $R^{22}$ are each independently H, a $C_{1-6}$ alkyl group, or $R^{21}$ and $R^{22}$ are optionally joined to form a $C_{1-4}$ alkylene group, or Y and Z are joined to form a —C(=O)—O— group or a —C(=O)—N($R^{20}$)— group ($R^{20}$ is H or a $C_{1-6}$ alkyl group).

6. The method according to claim 5, wherein Y is O and Z is a cyclopropyl group represented by the above-mentioned formula (VII).

7. The method according to claim 6, wherein $R^1$ is a methyl group.

8. The method according to claim 5 wherein the side effects are those due to an off-target effect.

9. A method of manufacturing an oligonucleotide with reduced side effects, comprising using one or more nucleic acid compound(s) represented by the following formula (I):

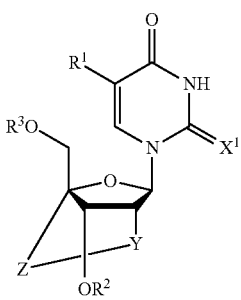
(I)

wherein $X^1$ is S or Se,

Y is a guanidino group represented by any of the following formulas (III)-(VI), and Z is a single bond or a $C_{1-4}$ alkylene group,

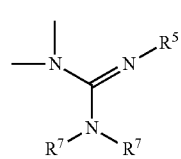
(III)

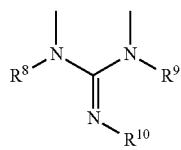
(IV)

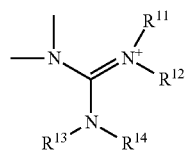
(V)

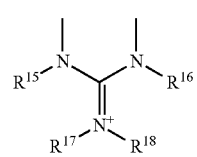
(VI)

wherein $R^5$-$R^{18}$ are each independently H, a $C_{1-6}$ alkyl group, a $C_{3-10}$ cycloalkyl group, an amino-protecting group or a 2-cyanoethyloxycarbonyl group, or Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the following formula (VII):

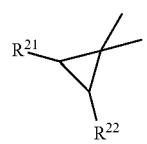
(VII)

wherein $R^{21}$ and $R^{22}$ are each independently H, a $C_{1-6}$ alkyl group, or $R^{21}$ and $R^{22}$ are optionally joined to form a $C_{1-4}$ alkylene group, or Y and Z are joined to form a —C(=O)—O— group or a —C(=O)—N($R^{20}$)— group ($R^{20}$ is H or a $C_{1-6}$ alkyl group), $R^1$ is H or a $C_{1-6}$ alkyl group, and $R^2$ and $R^3$ are each independently H, a hydroxyl-protecting group, or a phosphate group represented by the following formula (VIII):

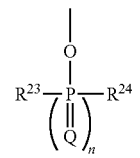
(VIII)

wherein Q is O or S, $R^{23}$ is H, a hydroxyl group, or a $C_{1-6}$ alkoxy group optionally substituted by a cyano group; $R^{24}$ is a hydroxyl group, a $C_{1-6}$ alkoxy group optionally substituted by a cyano group or an $NR^{25}R^{26}$ group wherein $R^{25}$ and $R^{26}$ are each independently H, a $C_{1-6}$ alkyl group or a 2-cyanoethyl group; and n is 0 or 1.

as a monomer to prepare the oligonucleotide according to claim 1.

10. The method according to claim 9, wherein Y is O and Z is a cyclopropyl group represented by the above-mentioned formula (VII).

11. The method according to claim 10, wherein le is a methyl group.

12. The method according to claim 9, wherein the side effects are those due to an off-target effect.

13. The oligonucleotide according to claim 1, wherein Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the above-mentioned formula (VII), or a pharmacologically acceptable salt thereof.

14. The method according to claim 5, wherein Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the above-mentioned formula (VII).

15. The method according to claim 9, wherein Y is O, S, an —N($R^{19}$)— group, a —C(=O)—O— group, a —C(=O)—N($R^{20}$)— group ($R^{19}$ and $R^{20}$ are each independently H or a $C_{1-6}$ alkyl group), and Z is a cyclopropyl group represented by the above-mentioned formula (VII).

\* \* \* \* \*